US009955909B2

(12) United States Patent
Flament (10) Patent No.: US 9,955,909 B2
(45) Date of Patent: May 1, 2018

(54) PROCESS FOR EVALUATION OF AT LEAST ONE FACIAL CLINICAL SIGN (71) Applicant: L'OREAL, Paris (FR)

(72) Inventor: Frédéric Flament, Paris (FR)

(73) Assignee: L'OREAL, Paris (FR)

( * ) Notice: Subject to any disclaimer, the term of this patent is extended or adjusted under 35 U.S.C. 154(b) by 0 days. days.

(21) Appl. No.: 15/104,011

(22) PCT Filed: Dec. 11, 2014

(86) PCT No.: PCT/IB2014/066803
§ 371 (c)(1),
(2) Date: Jun. 13, 2016

(87) PCT Pub. No.: WO2015/087274
PCT Pub. Date: Jun. 18, 2015

(65) Prior Publication Data
US 2017/0020436 A1 Jan. 26, 2017

(30) Foreign Application Priority Data
Dec. 12, 2013 (FR) ..................... 13 62468

(51) Int. Cl.
A61B 5/00 (2006.01)
G06F 3/16 (2006.01)
G06K 9/00 (2006.01)

(52) U.S. Cl.
CPC ............ A61B 5/442 (2013.01); A61B 5/0077 (2013.01); A61B 5/4803 (2013.01); G06F 3/167 (2013.01);
(Continued)

(58) Field of Classification Search
CPC ..... A61B 5/442; A61B 5/0077; A61B 5/4803; A61B 5/0062; A61B 5/1034; A61B 5/411;
(Continued)

(56) References Cited

U.S. PATENT DOCUMENTS 5,734,794 A * 3/1998 White ................... G09B 5/065
704/235
6,721,001 B1 4/2004 Berstis
(Continued)

FOREIGN PATENT DOCUMENTS

EP 0699941 A1 3/1996
EP 1216658 A1 6/2002
(Continued)

OTHER PUBLICATIONS

International Search Report for PCT/IB2014/066803 dated Apr. 13, 2015 (4 pages).
(Continued)

Primary Examiner — Ruiping Li
(74) Attorney, Agent, or Firm — Shumaker, Loop & Kendrick, LLP (57) ABSTRACT The present invention relates to a process without a therapeutic target that evaluates at least one facial clinical sign and/or evaluates make-up, in particular evaluates wrinkles or fine lines from a portion of the face, including steps consisting in: —from a sequence of facial images of a person filmed while emitting at least one sound, extract from the sequence one or more images coinciding with the emission of at least one predefined sound, —from the resulting image or images extracted, evaluate at least one facial clinical sign appearing on the image or images extracted and/or evaluate at least one characteristic related to make-up.

20 Claims, 3 Drawing Sheets (52) U.S. Cl.
CPC ..... *G06K 9/00255* (2013.01); *G06K 9/00281*
(2013.01); *G06K 9/00288* (2013.01)

(58) Field of Classification Search
CPC ........... G06K 9/00288; G06K 9/00255; G06K
9/00281; G06F 3/167; A45D 44/005
See application file for complete search history.

(56) References Cited

U.S. PATENT DOCUMENTS

| | | |
|---|---|---|
| 7,023,454 B1 | 4/2006 | Knight |
| 2002/0090123 A1 | 7/2002 | Bazin |
| 2003/0063801 A1 | 4/2003 | Rubinstenn et al. |
| 2003/0065278 A1 | 4/2003 | Gilles Rubinsten et al. |
| 2008/0112968 A1 | 5/2008 | Gebicki |
| 2014/0205159 A1* | 7/2014 | Yoshida ............... A61B 5/0077 382/118 |

FOREIGN PATENT DOCUMENTS

| | | | |
|---|---|---|---|
| EP | | 2503545 A1 | 9/2012 |
| JP | | 2005-65812 A | 3/2005 |
| JP | | 2009-61178 A | 3/2009 |

OTHER PUBLICATIONS

Written Opinion for PCT/IB2014/066803 (5 pages).
Japanese (JP) Office Action for JP 2016-538578 dated May 29, 2017 (4 pages total including English translation).

* cited by examiner

PROCESS FOR EVALUATION OF AT LEAST ONE FACIAL CLINICAL SIGN

TECHNICAL FIELD AND BACKGROUND

The present invention relates to the evaluation of characteristics of body type, and more specifically face type, and the evaluation of products for making up or changing the appearance of the face.

There is an advantage in evaluating all of the clinical signs describing a face, in particular to measure how they vary with age or under the effect of a cosmetic treatment and to understand the perception that the consumer has of the treatment.

Currently this evaluation occurs using atlases used by experts or clinicians or using morphings, as described in patent application EP 1 216 658 in the name of the Applicant.

In application FR 2 935 593 one proposal was to compare the appearance of some characteristics according to its severity.

BRIEF SUMMARY

The existing evaluation processes are not entirely satisfactory since they do not take into account facies deformations during daily or physical activity and their impact on apparent age or attractiveness. Accordingly, for example, a person aged between 30 and 40 years old may appear close to 30 years old on a passport photo but with movement, facial features may be estimated at closer to 40 years old.

There is also a need to perfect the processes for evaluating facial clinical signs (also called appearance characteristics) such as wrinkles, in particular under-eye wrinkles, crows' feet wrinkles, the nasolabial fold, the forehead, the corners of the lips, the upper lip, etc.

There is also an advantage in evaluating how a make-up holds or how well a make-up product can hide some flaws, and more generally in assessing the effect of a cosmetic treatment on the face's appearance and how it changes over time.

The invention aims to answer this need or these needs and achieves this through a process without a therapeutic target that evaluates at least one facial clinical sign, in particular wrinkles or fine lines on a part of the face, and/or evaluates a make-up, including the steps consisting of:
  from a sequence of facial images of a person filmed while emitting at least one sound, extract from the sequence one or more images coinciding with the emission of at least one predefined sound,
  from the image or images extracted, evaluate at least one facial clinical sign appearing on the image or images extracted and/or evaluate at least one characteristic related to make-up.

Preferably, image extraction is automatic, resulting from an analysis of the sound emitted, to automatically recognize it.

"Extracting" an image is understood to mean that the image is identified in the sequence with a view to subsequent treatment; the image may remain in the sequence and be identified for example by a time stamp or an order number in the sequence. The image is not necessary duplicated or transferred into another electronic file. The sequence is preferably a digitized sequence, in any format suited to reading by a multimedia content reader, for example an HD video format. It may be advantageous to display the images extracted, so that the person can see them. When the evaluation is made at a point of sale, this can also make it easier to advise the person.

The invention can account for the fact that when a face moves the facial features, wrinkles or fine lines change and/or flex and appear differently for each person. These facial deformation modes that are not perceptible on a simple static image become perceptible due to this process. Accordingly, it allows precise evaluation of clinical signs of ageing for facial skin in particular.

The invention can also show the first signs of ageing, for example for Asian or Caucasian women between 30 and 40 years old, which appear only when the face is animated, when the person is going to talk.

By selecting the images that correspond to the person's predefined sound emissions the evaluation can be standardized and automated.

Accordingly, due to the invention, it is possible to easily select the images that always relate to the same deformation for all people, regardless of the measurement time.

To acquire the sequence of images, at least one sound to be reproduced can be displayed in front of the person filmed, for example a phrase, scansion, word, phoneme, chosen for example as a function of the language that the person speaks, which can for example be French, English, Spanish, Japanese, Chinese or Korean. This display can be on the same device as the one that films, which can allow the image displayed to be known as a function of time in the sequence, and can facilitate the location of the image or images of interest in the sequence. As a variant, the sound is diffused using a speaker for example, then repeated by the person. The person is filmed at the same time as the sound is recorded, to generate the sequence with a video track and an audio track.

The person may be asked to pronounce the same sounds several times, but within sound sequences where the sounds are not in the same order. This can make differences related to different facial deformation modes appear, according to the order in which the sounds are emitted.

For the evaluation, the images extracted may be compared with reference images. Preferably, this comparison is made automatically, through image processing. Any process that can compare images may be used, for example a process called fuzzy logic. A recognition for characteristic features on an image can also be used. In this case, the program may have to learn at first so that it knows what score the different images correspond to. Then the program knows how to attribute a score to any new image itself. A neural network can be used. The publications "*Automatic Breast Lesion Segmentation and Scoring in Color Alastography Images*", N. Gupta and S. Kudavelly, Philips Electronics India Limited, Bangalore, "*Methodes d'apprentissage statistique pour le scoring*" [Statistical Learning Methods for Scoring], Marine Depecker, Ecole Nationale Supérieure des Télécommunications, France, "*Scoring diverse cellular morphologies in image-based screens with iterative feedback and machine learning*", Thouis R. Jones, Anne E. Carpenter, Michael R. Lamprecht, Jason Moffat, Serena J. Silver, Jenniver K. Grenier, Adam B. Castoreno, Ulrike S. Eggert, David E. Root, Polina Golland, David M. Sabatini, Proceedings of the National Academy of Sciences, Vol. 106, No 6 (Oct. 2, 2009), pages 1826-1831 and "*Automated breast cancer detection and classification using ultrasound images: A survey*" H. D. Cheng, Juan Shan, Wen Ju, Yanhui Guo, and Ling Zhang. Pattern Recognition 43(1): 299-317 (2010), describe examples of such recognition processes.

The previously cited reference images may be images from an evaluation atlas, or from data generated from such images. The atlas' images are for example images of people presenting different grades of a given clinical sign, for example a given facial region that appears more and more wrinkled.

The sequence that is treated may include images relating to any clinical sign at all that is revealed when the person speaks, for example the presence of wrinkles or fine lines in the corners of the lips, under the eye, on the upper lip, crows' feet, and/or the nasolabial fold. The sequence preferably includes images of the entire face, the face being preferably filmed with sufficient resolution to be able to subsequently extract images of regions of interest that only represent a fraction of the camera's field of view. Colorimetry correction may be applied.

Preferably, the evaluation of the clinical sign or signs from the image or images extracted occurs automatically, by comparison with reference data. During this automatic evaluation, the image or images extracted are, at least for some, automatically cropped as a function of the clinical sign to be evaluated, and preferably enlarged.

The image sequence may include several different sounds emitted successively by the person, in particular at least five different sounds, in particular chosen from "A"=a, "E"=ə, "O"=o, "OUI"='wi, "STI"=sti:, "ART"=aR, "TO"=tɔ. They may be simple sounds, pronounced with a moment of silence between them, or sounds corresponding to saying a phrase. The sound or sounds in the sequence may include predefined phonemes, chosen for example as a function of the language that the person speaks, for example vowels, semi-consonants or consonants. The images corresponding to several predefined sounds respectively are extracted, in particular the previously cited sounds "A", "E", "O", "OUI", "STI", "ART", "TO".

The selection of the image or images to be extracted from the sequence may occur by voice recognition applied to the soundtrack of the sequence and/or by spectral analysis of the sounds collected. Another possible selection is images for which a specific frequency exceeds a predefined amplitude.

A score associated with a clinical sign can automatically be generated as a result of the evaluation of this clinical sign.

The images may be acquired by a device held by the person being evaluated or placed in front of him/her, in particular a tablet, smart phone or computer. For example, the person downloads an application onto his or her smartphone, for example iPhone or Android smartphone, tablet, or PC. Once the application is launched, it displays sounds to be reproduced on the monitor while it records the images and sounds. The user can then film him or herself while pronouncing the predefined sounds. The sequence thus acquired is then treated as indicated above to produce an evaluation result. The treatment may take place locally, through the application itself, or as a variant on a remote server, or partially locally and partially at the remote server.

The acquisition may occur simultaneously with several cameras.

The evaluation may take place in a home or at a point of sale.

The acquisition of the sequence of images occurs at an acquisition frequency greater than or equal to 50, preferably 100, images per second. The camera resolution is preferably greater than or equal to 720 lines. Several curves of how the score progresses for a given clinical sign can be generated as a function of the order in which the sounds are emitted.

In parallel with the automatic evaluation of the clinical sign, a self-assessment score can be collected by the person for said clinical sign and/or an evaluation score is collected by a panel of experts for said clinical sign.

The invention also relates to a non-therapeutic process to demonstrate the effect of a cosmetic treatment on the face, in particular the application of an anti-wrinkle or make-up product, including the steps consisting in:
- make a first evaluation, in particular of at least one facial clinical sign, using the evaluation process according to the invention, as defined above,
- make a new evaluation, in particular after a facial cosmetic treatment,
- compare the evaluations,
- generate representative information about treatment efficacy from comparison of evaluations and/or representative of the change in the make-up between said evaluations.

The cosmetic treatment consists for example in applying a skincare or anti-wrinkle product to the skin, in particular in the area affected by the evaluation.

The person evaluated can see him or herself automatically prescribed a product as a function of the scores determined, as a preventive measure or to reduce the severity of a sign. The product prescribed may be a personalized formulation, with for example an active ingredient assay that depends on the score or scores determined.

The invention further relates to a computer program product including instructions that, when executed on a device that has a processor, a monitor, a speaker, a camera and a microphone, lead the device to:
- optionally, display on the monitor a sound to reproduce, and/or emit the sound using the speaker,
- acquire a sequence of images of a person reproducing a predefined sound using the camera, in particular the sound that is displayed and/or diffused,
- treat the images acquired to extract from the sequence of images acquired the image or images for which the sound emitted by the person corresponds to the said predefined sound.

The instructions may if need be allow prior selection of the sound or sounds that must be recognized by the device.

The instructions may also lead the device to propose that the user chooses one or more clinical signs to evaluate; in this case, as a function of the sign or signs selected, the predefined sound or sounds that the person must pronounce for the evaluation may differ.

The instructions may lead the device to analyse the sound emitted with a view to recognizing it, in particular by a voice recognition technique. The images extracted are then those for which the predefined sound is automatically recognized, within the corresponding audio track.

The instructions may also lead the device to process the resulting image or images extracted to generate at least one representative score of the severity of the clinical sign and/or to send the image or images to a remote server that in return delivers said score.

The instructions may also control a device that makes an automatic assay for active ingredient in a treatment, in particular an anti-wrinkle treatment, as a function of said score.

BRIEF DESCRIPTION OF THE DRAWINGS

The invention may be better understood on reading the following description of non-limiting implementation examples thereof, and with reference to the attached drawing, in which.

DETAILED DESCRIPTION

Figure 1:
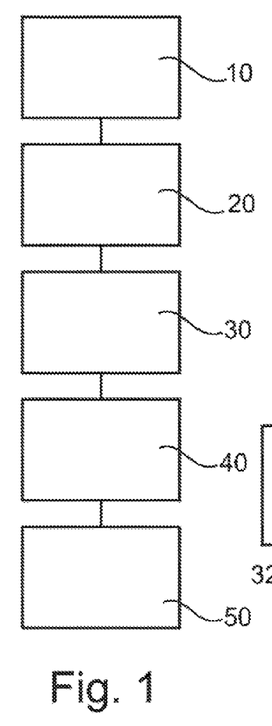
FIG. 1 is a block diagram illustrating steps of an example of the process according to the invention.

An example of the process according to the invention may use, as illustrated in FIG. 1, different steps 10 to 50, which are taken for example using a computer equipped with a camera and a monitor. The camera is preferably calibrated colorimetrically, by placing a calibrator whose colorimetric components are known in the camera's field of view.

At step 10, a video sequence is acquired using the camera. While this sequence is being acquired, the sounds that the person being filmed must reproduce are for example displayed on the monitor. As a variant, nothing is displayed while the sequence is being acquired, and the person knows for example in advance which sounds he or she must pronounce.

Next, the image sequence is analysed in step 20. This analysis may be as post-processing, or as a variant, while the sequence is being recorded, on the images already acquired, if the processor is powerful enough to do this.

The treatment aims to identify in the sequence the image or images that correspond to the emission by the person of predefined sounds. To identify the images to which the sounds correspond, the soundtrack is analysed and the instants where the predefined sounds are emitted are identified, using for example spectral analysis, where each sound has its own spectral fingerprint that is to be identified in the soundtrack. The spectral fingerprint can be obtained by Fourier transformation. Voice recognition software can also be used. The publications *"Voice Activity Detection Based on Wavelet Packet Transform in Communication Nonlinear Channel"*, R. Chiodi and D. Massicotte, SPACOMM, Colmar, France, 2009 and *"La reconnaissance automatique de sources sonores dans l'environnement"* [Automatic recognition of noise sources in the environment], Defreville, B. Bloquet, S., Filippi, G., and Aujard, $10^{ème}$ Congrès Français d'Acoustique [10th French Acoustical Conference], Lyons 12-16 Apr. 2010, describe examples of voice recognition processes.

To increase the robustness of the recognition, it is possible to combine a classic voice recognition algorithm such as that used in smartphones with an analysis by recognition of a frequency pattern associated with each phoneme.

Figure 2:
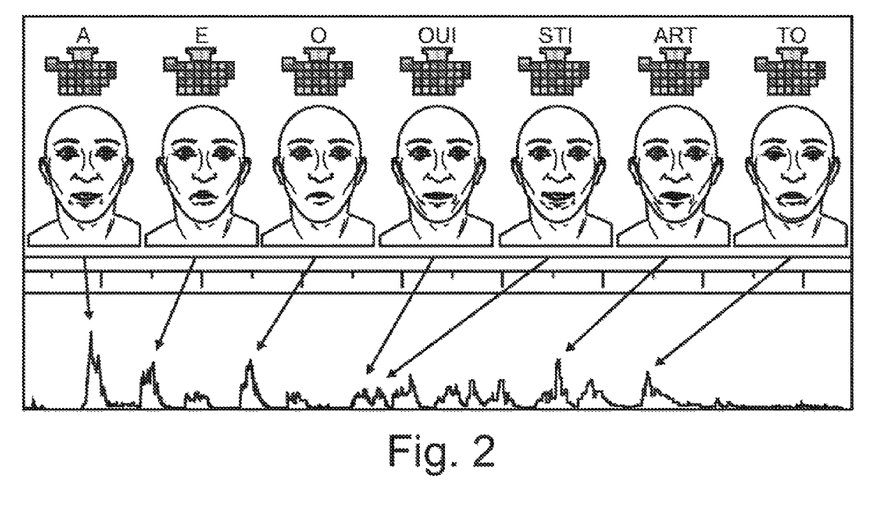
FIG. 2 represents images extracted from a sequence of images of a person filmed while pronouncing different sounds.

In the example in FIG. 2, the person being filmed pronounces an entire phrase comprising the words OUIstiti, smARTies, etc. and thereby successively emits the sounds "A", "E", "O", "OUI", "STI", "ART", "TO". The images that are selected as corresponding to the emission of these sounds are represented on this figure under each sound, along with the sound's spectral fingerprint and the time stamp.

In step 30, each image extracted that corresponds to a predefined sound can be processed with a view to evaluating one or more clinical signs.

Figure 3:
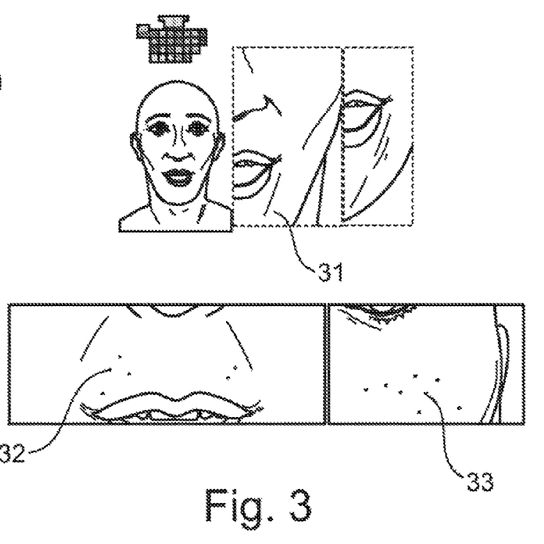
FIG. 3 represents different images corresponding to areas of interest and/or different degrees of enlargement.

The processing in step 30 may include the extraction of areas of interest in the image, for example by recognizing characteristic features in the image, such as the presence of eyes, nose or lips. From this sub-images can be generated that cover more specifically the areas of interest containing the clinical sign or signs that the evaluation targets. As illustrated in FIG. 3, for example from a complete image of the face corresponding to the emission of a particular sound, respective sub-images 31 to 33 of the corners of the lips, the upper lip and the under-eye area can be extracted.

These sub-images may be enlarged, if need be, to make wrinkles or fine lines appear more clearly. It is also desirable to adjust the colorimetry if necessary, to remove the influence of tanning, for example.

Next a treatment is carried out in step 40 to compare these images to reference images, with a view to attributing a grade to the clinical sign supposed to appear on the image.

This treatment may involve any algorithm that can compare the degree to which two images resemble each other, i.e. the image whose reference grade needs to be allocated, and the images illustrating the different grades. For the learning programme that attributes a score automatically, a reference database can be used that gives the scores for a large number of different people, for ethnicity for example.

Finally, in step 50, a score and/or any useful information related to the clinical sign whose severity was evaluated can be displayed. The score is for example displayed on the monitor.

A curve can also be displayed that makes the score for the clinical sign appear as a function of facial deformations related to the sounds pronounced. Accordingly, information on the dynamics of the sign's change for a moving face are available; this can provide additional useful information, in combination if need be with other dynamic change in other clinical signs, to attribute to the person for example an apparent age or an apparent level of fatigue.

For each clinical sign considered, different 2D-curves can be created as a function of the order of the sounds considered.

Accordingly for under-eye wrinkles, for example, progression curves and 2D-matrices of the curves can be generated automatically for the score for sounds X1, X6, X8, etc., sounds X8, X4, X10, X4, etc., sounds X1, X3, X4, X8, etc. Each of these sequences of sounds emitted by the person to be evaluated will have been chosen to maximize some deformation modes or to be able to reconstruct a given phrase. From this step, spectra can be treated by 2D or 3D wavelets related to the person's perception or consumers' perception, for a set of clinical signs, collected by video quizzes for different phrases or sounds.

The sub-image treatment processing can also be completed if need be by more conventional analysis such as detection of skin dyschromia or pore size evaluation.

Figure 4:
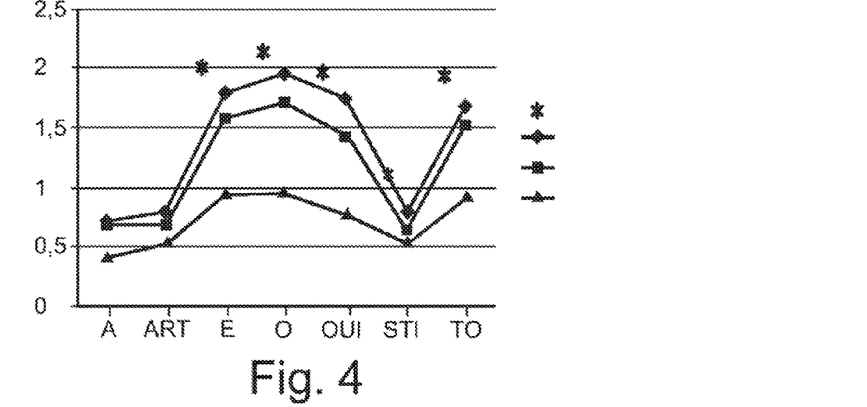
FIGS. 4 to 6 represent examples of score progressions for a given clinical sign as a function of the sound pronounced.
Figure 5:
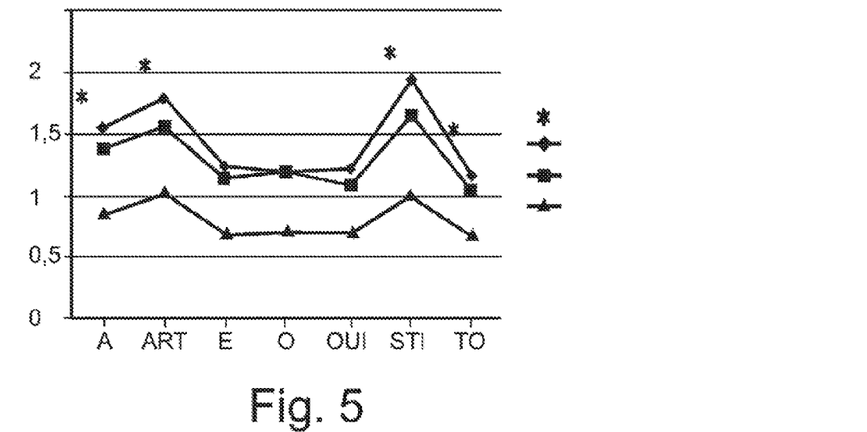
Figure 6:
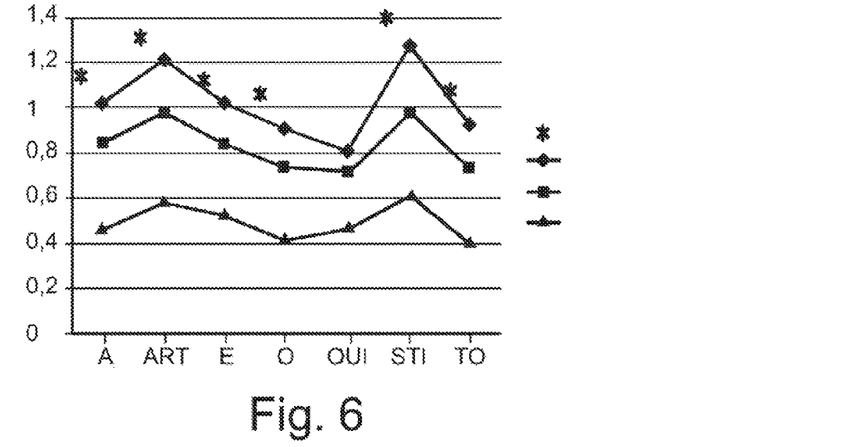

The results of the experiments are now described, referring to FIGS. 4 to 6.

In FIG. 4 the change in the severity score for upper lip wrinkles has been represented as a function of the sound pronounced, here "A", "E", "O", "OUI", "STI", "ART", "TO", for panels of 25 women each, i.e. a panel of women 37 years old on average before treatment by applying a product for twice-daily use for one month (diamonds), a panel of women 32 years old on average (triangles), and the same 37-year old women after treatment by applying the product (squares). The * marks the sounds for which the results are significant. We see that the invention can only be used to show the effect of the product when certain sounds are pronounced, for example the sound O. The differences before and after treatment are then significant and highly visible. The two different age groups can be differentiated for all the sounds.

FIGS. 5 and 6 relate to the evaluation of the severity of the nasolabial fold and under-eye wrinkles respectively.

Depending on the area and/or clinical sign, the dynamic progressions are different. A simple translation of value for the score may be observed for the nasolabial fold or under-eye wrinkles (FIGS. 5 and 6), yet different deformation modes are seen in 5 years for lip wrinkles (FIG. 4). Wrinkles at the corners of the lips, though statistically different for the two age groups, have a much lower dynamic.

Various statistical and mathematical analyses may be applied to the data from using the process according to the invention.

Figure 7:
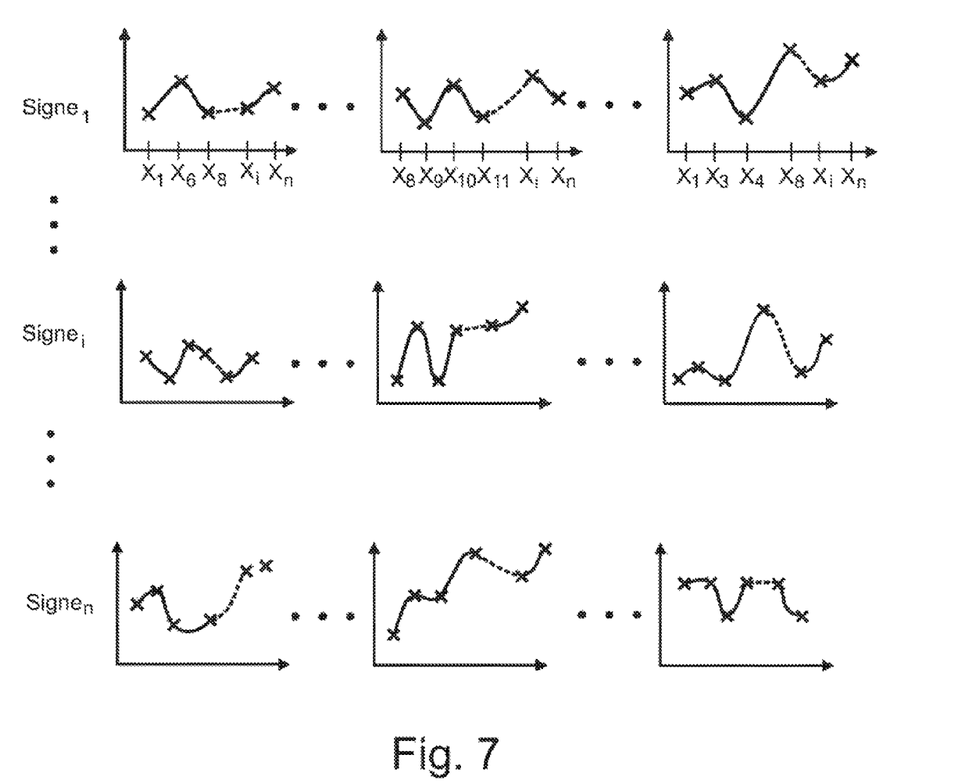
FIG. 7 represents different score progressions for different clinical signs, as a function of the sounds pronounced, allowing a 2D-plot matrix to be processed.

For example, as illustrated in FIG. 7, from the understanding of different scores S1 to Sn for a clinical sign $Sign_i$, for example different sounds X1 to Xn, 2D matrices of time curves can be generated that represent the progression in different scores as a function of the sounds emitted over time for various clinical signs.

From a consumer study the perception associated for each person evaluated can be determined, for example in terms of apparent fatigue, apparent age, attractiveness, radiance, etc.

All the curves resulting from the evaluation of these people can then be analysed to show the relationship between some curve shapes and the corresponding perception in terms of apparent fatigue, apparent age, etc.

Multi-scale wavelets can be used to perform these multi-scale treatment analyses, for example.

The invention is not limited to the examples that have just been described. For example the person to be evaluated can be filmed in profile with a view to evaluating other clinical signs such as ptosis, for example. The images may also be acquired, if need be, in relief using at least two cameras. The images may also be acquired with projection of fringes of light on the face to further measure relief or better visualize skin movements. The images can be acquired with white light or under an illuminant that has the purpose of more easily showing certain facial deformations when the sounds are emitted.

When several images are combined with an emitted sound, these images may be averaged before the treatment that will attribute a score.

If need be, the person for whom evaluation is sought pronounces one or more phrases where the content is not known in advance; in this case the process seeks to recognize by voice recognition whether certain sounds have been produced, and in the affirmative selects the corresponding images then evaluates the clinical signs.

Another possible plan is to select a set of sounds for the person to pronounce for which evaluation is desired as a function of the sex, apparent age, ethnicity, so that he or she can be led to pronounce sounds that better show the clinical signs for which evaluation is desired.

Although it is preferable that image extraction be automatic after the automatic detection of the sound emitted, which is thus recognized by the program being executed, the image extraction may occur without automatic recognition of the sound emitted, taking the hypothesis that on the images of the sequence having a predefined temporal position on the sequence the person is emitting the sound, for example because this is displayed on the monitor and the person must emit the sound when it is displayed.

The invention may be used on bare skin, before or after a skincare treatment such as an anti-wrinkle treatment.

The invention may also be used on made up skin, for example by applying a foundation or a patch to correct a flaw, for example to change the shape of the expression.

This can allow the hold of a make-up and its effect on facial appearance to be evaluated during deformations. This may also allow evaluation of make-up visibility as a function of facial deformations.

The expression "including a" is synonymous with "including at least one".

The invention claimed is:

1. A method to evaluate at least one facial clinical sign, comprising:
   from a digitized sequence of facial images of a person filmed while emitting at least one sound, extract, with a device with a processor, one or more images coinciding with the emission of at least one predefined sound, the image extraction being performed automatically based on an analysis by the device of the sound emitted;
   from the resulting image or images extracted, evaluate, with the device with the processor, at least one facial clinical sign appearing on the image or images extracted, the evaluation comprising comparing automatically by the device the images extracted with reference images.

2. The method according to claim 1, wherein the image extraction comprises selecting image by voice recognition applied to a soundtrack of the sequence and/or by spectral analysis of the sounds collected, or selecting images for which a specific frequency exceeds a predefined amplitude.

3. The method according to claim 1, wherein at least one sound to reproduce is displayed in front of the person filmed.

4. The method according to claim 1, wherein the images extracted are compared with reference images.

5. The method according to claim 1, wherein the sequence includes images concerning the presence of wrinkles or fine lines at the corners of the lips, under the eye, the upper lip, crow's feet, and/or the nasolabial fold.

6. The method according to claim 5, the sequence including images of the entire face.

7. The method according to claim 1, wherein the evaluation of the clinical sign or signs from the image or images extracted occurs automatically, by comparison with reference data.

8. The method according to claim 1, wherein the image or images extracted are, at least for some, automatically cropped as a function of the clinical sign or signs to be evaluated.

9. The method according to claim 1, wherein the sequence of images includes several different sounds emitted successively by the person and in which the images corresponding respectively to several predefined sounds are extracted.

10. The method according to claim 1, including at least five different sounds.

11. The method according to claim 9, the sound being selected from "A", "E", "O", "OUI", "STI", "ART" and "TO".

12. The method according to claim 1, wherein the sound or the sounds of the sequence include phonemes.

13. The method according to claim 1, wherein the selection of the image or images to be extracted occurs by voice recognition applied to the soundtrack of the sequence and/or by spectral analysis of the sounds collected.

14. The method according to claim 1, wherein a score associated with each of the at least one clinical sign is automatically generated as a result of the evaluation of this clinical sign.

15. The method according to claim 1, wherein the images are acquired by a device held by the person being evaluated or placed in front of said person.

16. The method according to claim 1, wherein the acquisition of the images of the sequence occurs at an acquisition frequency greater than or equal to 50, images per second.

17. The method according to claim 14, wherein several curves of how the score progresses for a given clinical sign of the at least one clinical sign are generated as a function of the order in which the sounds are emitted.

18. The method according to claim 1, wherein, in parallel with the automatic evaluation of the clinical sign or signs, a self-assessment score is collected by the person for said clinical sign or signs and/or an evaluation score is collected by a panel of experts for said clinical sign or signs.

19. A method to demonstrate the effect of a cosmetic treatment on the face, comprising:
- make a first evaluation of at least one facial clinical sign, using the method as defined in claim 1,
- make a new evaluation, after a facial cosmetic treatment, compare the evaluations,
- generate representative information about treatment efficacy from comparison of evaluations.

20. A method to evaluate make-up, comprising:
- extract, with a device with a processor, from a digitized sequence of facial images of a person filmed while emitting at least one sound, one or more images coinciding with the emission of at least one predefined sound, the image extraction being performed automatically based on an analysis by the device of the sound emitted;
- from the resulting image or images extracted, evaluate, with the device with the processor, the hold of a make-up and its effect on facial appearance to be evaluated during facial deformations, and/or make-up visibility as a function of facial deformations, the evaluation comprising comparing automatically by the device the images extracted with reference images.

* * * * *

UNITED STATES PATENT AND TRADEMARK OFFICE
CERTIFICATE OF CORRECTION

PATENT NO. : 9,955,909 B2
APPLICATION NO. : 15/104011
DATED : May 1, 2018
INVENTOR(S) : Frederic Flament It is certified that error appears in the above-identified patent and that said Letters Patent is hereby corrected as shown below:

In the Claims

Column 10, Line 14, after "facial appearance" delete "to be evaluated".

Signed and Sealed this
Ninth Day of July, 2019

Andrei Iancu
*Director of the United States Patent and Trademark Office*